(12) United States Patent
Murigneux et al.

(10) Patent No.: US 8,330,006 B2
(45) Date of Patent: *Dec. 11, 2012

(54) MAIZE WITH GOOD DIGESTIBILITY AND DISEASE RESISTANT

(75) Inventors: Alain Murigneux, La Roche Blanche (FR); Christophe Tatout, Salt en Donzy (FR); Jean-Pierre Martinant, Vertaizon (FR); Bruno Grezes-Besset, Colomiers (FR)

(73) Assignee: Biogemma, Paris (FR)

( * ) Notice: Subject to any disclaimer, the term of this patent is extended or adjusted under 35 U.S.C. 154(b) by 654 days.

This patent is subject to a terminal disclaimer.

(21) Appl. No.: 12/447,086

(22) PCT Filed: Oct. 23, 2007

(86) PCT No.: PCT/EP2007/061373
§ 371 (c)(1),
(2), (4) Date: Jun. 23, 2009

(87) PCT Pub. No.: WO2008/049849
PCT Pub. Date: May 2, 2008

(65) Prior Publication Data
US 2010/0005537 A1    Jan. 7, 2010

(30) Foreign Application Priority Data

Oct. 24, 2006 (FR) .................... 06 09295

(51) Int. Cl.
*A01H 1/00* (2006.01)
*A01H 1/02* (2006.01)
*A01H 5/00* (2006.01)
*C12N 15/82* (2006.01)

(52) U.S. Cl. ............ 800/320.1; 800/260; 800/298; 800/275; 800/265; 426/18

(58) Field of Classification Search ............ None
See application file for complete search history.

(56) References Cited

U.S. PATENT DOCUMENTS

| | | | |
|---|---|---|---|
| 5,728,570 A | 3/1998 | Matern et al. | |
| 6,160,205 A | 12/2000 | Matern et al. | |
| 6,211,432 B1 | 4/2001 | Boudet et al. | |
| 8,013,214 B2 | 9/2011 | Murigneux et al. | |
| 8,115,054 B2 * | 2/2012 | Tatout et al. | 800/279 |
| 2010/0146658 A1 | 6/2010 | Tatout et al. | |
| 2011/0252500 A1 | 10/2011 | Murigneux et al. | |

FOREIGN PATENT DOCUMENTS

| | | |
|---|---|---|
| EP | 0516958 A2 | 12/1992 |
| EP | 1000543 A1 | 5/2000 |
| WO | WO-93/05159 A1 | 3/1993 |
| WO | WO-93/05160 A1 | 3/1993 |
| WO | WO-97/12982 A1 | 4/1997 |
| WO | WO-99/10498 A2 | 3/1999 |
| WO | WO-99/24561 A2 | 5/1999 |
| WO | WO-2006/035045 A1 | 4/2006 |

OTHER PUBLICATIONS

Anterola, Trends in lignin modification: a comprehensive analysis of the effects of genetic manipulations/mutations on lignification and vascular integrity, Phytochemistry, vol. 61, 2002, pp. 221-294.

Bily et al., Dehydrodimers of Ferulic Acid in Maize Grain Pericarp and Aleurone: Resistance Factors to *Fusraium graminearum*, Phytopathology, vol. 93, No. 6, 2003, pp. 712-719.

Boudet et al., Lignin genetic engineering, Molecular Breeding, vol. 2, pp. 25-39, 1996.

Fofana et al., Suppression of Induced Resistance in Cucumber Through Disruption of the Flavonoid Pathway, Phytopathology, vol. 95, No. 1, 2005, pp. 114-123.

Lamb et al., Emerging Strategies for Enhancing Crop Resistance to Microbial Pathogens, Biotechnology, vol. 10, Nov. 1992, pp. 1436-1445.

* cited by examiner

*Primary Examiner* — Medina A Ibrahim
(74) *Attorney, Agent, or Firm* — Connolly Bove Lodge & Hutz LLP

(57) ABSTRACT

The present invention relates to the field of the improvement of the digestibility and the tolerance of maize to fungal pathogens and especially to fusariosis by modification of the C4H gene.

15 Claims, 2 Drawing Sheets

MAIZE WITH GOOD DIGESTIBILITY AND DISEASE RESISTANT

RELATED APPLICATIONS

This application is a national stage application (under 35 U.S.C. §371) of PCT/EP2007/061373, filed Oct. 23, 2007, which claims benefit of French application 0609295, filed Oct. 24, 2006.

FIELD OF THE INVENTION

The present invention relates to the field of the improvement of plants, in particular the improvement of the digestibility of maize, and of the tolerance of maize to fungal pathogens and especially to fusariosis.

More precisely, the present invention relates to the development of a particular allele of the gene coding for an isoform of cinnamate-4-hydroxylase or C4H (EC 1.14.13.11) in maize. The presence of this allele results in an improvement in the digestibility and the tolerance to fusariosis relative to an isogenic maize not possessing the allele. The quantity of lignin present in the plant is also decreased.

BRIEF SUMMARY OF THE INVENTION

Lignin, together with cellulose, is one of the two major components of the plant wall. The plant wall, mainly consisting of cellulose, hemi-cellulose and lignin, provides the cell with a natural barrier against the exterior. Many studies have shown that one of the responses to biotic stress (pathogen attack) or abiotic stress (drought, wind . . . ) consists in reinforcement of the plant wall in particular by a greater content of lignins. Moreover, many agronomic or industrial sectors see their yields directly linked to the lignin content and/or to the lignin composition of the wall, in particular the paper industry, the production of fuels (in particular biomass intended for biofuels) or the production of silage.

For example, the quality of silage maize can be improved by decreasing the lignin content or by modifying its composition. Maize silage is an important food: the yield in the field is relatively high, harvesting and storage are easy, and the nutritional qualities are stable and can easily be supplemented in proteins by other fodder silages or by soya oil cakes. An experiment carried out by Emile (1995, Annales de zootechnie) shows that feeding livestock with a more digestible maize makes it possible to increase the daily milk production and the weight gain relative to a food with a less digestible maize. The optimization of the qualities of maize silage thus consists in increasing the net energy provided by this type of food by improving its digestibility and therefore by decreasing the lignin content.

Thus, the selection or the obtention of more digestible maize plants, in particular those in which the lignins biosynthesis pathway is modified is one of the favored areas for maize improvement. It is nonetheless necessary that the plants selected have good yields and be of low susceptibility to various stresses (mechanical, water . . . ).

Moreover, the maizes are subject to attack by many pathogens, among them viruses and bacteria, but also fungal pathogens, responsible for many diseases, and sometimes for the presence of mycotoxins.

Thus, maize can be attacked by the fungi responsible for fusariosis (due to *Fusarium*, including *F. roseum*, *F. graminnearum*, *F. liseola* and *F. monoliforme*), smut (common or of the inflorescences, due to *Ustilago zeae* or *Ustilago maydis*), anthrachnosis (*Colletotrichum graminicola*), kabatiellosis, helminthosporosis (*Helmninthosporium turcicum*), rust (*Puccinia maydis*) and mildew. In general, fungal attacks are responsible for desiccation and/or rotting of the plants, at different locations depending on the pathogen.

The fungi of the *Fusarium* genus are responsible for fusariosis. The species *F. graminearum* and *F. monoliforme*, which are pathogenic to maize and whose importance varies depending on the climatic conditions and the precocity of the maize varieties, may be cited. Fusariosis of the cob can be distinguished from fusariosis of the stem, the infection processes being very different. However, certain pathogenic agents are common to both types of fusariosis.

Fusariosis of the cob which results in the destruction of the grains decreases the yield of the maize crops. The pathogenic agents responsible are very detrimental in other respects since they accumulate in the grains, whether or not destroyed, various mycotoxins (zearalenone, deoxynivalenol, fumonisins) which exhibit toxicity levels varying depending on the animal species and are difficult to eliminate.

Fungicidal treatments are difficult to use and only have a limited effect against the *Fusaria*. The best way of combating fusariosis of the cob is the use of genetic resistance. At present, few hybrids possess such resistance, and when it does exist it is partial resistance, which remains moderate.

The present application shows that the inhibition of the C4H gene and in particular the presence of the D1938 allele of the maize C4H gene makes it possible to obtain a maize which is at the same time more digestible and presents better tolerance to fungal diseases, and especially to fusariosis.

Fungal diseases are caused by fungal pathogens such as those described above.

It is difficult to know how to modify the lignins biosynthesis pathway and to foresee what the consequences of the modifications will be. In fact the lignins biosynthesis pathway remains a complex pathway, involving a large number of enzymatic reactions (Dixon et al., 2001, Phytochemistry, 57(7), 1069-1084), and whereof the possible compensation mechanisms are still imperfectly elucidated.

Lignin is considered to be an insoluble polymer of 3 monomers of alcohols or monolignols: p-coumaryl alcohol (H subunits), coniferyl alcohol (G sub-units) and sinapyl alcohol (S subunits), derived from the phenylpropanoid pathway (Neish, 1968, Constitution and Biosynthesis of lignin, eds New York, Springer Verlag 1-43). Each type of precursor can form a variety of bonds with others and thus constitute the lignin. Other bonds can also form with other wall compounds (polysaccharides and proteins) to form a complex three-dimensional network.

The main steps in the production of lignin are hydroxylation and O-methylation of the aromatic rings then the conversion of the carboxyl side-chain into an alcohol group.

The current hypothesis for the biosynthesis pathway for the monolignols considers that the metabolic network leading to the formation of the S and G subunits involves successive hydroxylation and O-methylation reactions at different oxidation levels of the side-chain. The enzymes of the network include:

- distinct O-methyltransferases: caffeic 3-O methyltransferase (COMT), also called 5-hydroxy-coniferyl aldehyde O-methyltransferase (AldOMT) and caffeoyl coenzyme A 3-O methyltransferase (CCoAOMT)
- hydroxycinnamate coenzyme A ligases (4CL)
- one or more cytochrome P450 ferulate 5-hydroxylases (F5H)
- and several isoforms of cinnamoyl CoA reductase (CCR) and cinnamyl alcohol dehydrogenase (CAD).

The properties of these different enzymes have been the subject of reviews (Boudet et al, 1995 New Phytol. 129, 203-236; Dixon et al, 2001, previously cited; Whetten et al., 1998 Annu Rev. Plant Physiol Plant Mol Biol, 49, 585-609, and Li et al., 2000 J. Biol Chem, 275, 6537-6545).

For several years, attempts have been made to modify the lignins content and composition of plants by overexpressing or underexpressing one or more genes of the lignins biosynthesis pathway (Anterola and Lewis, 2002, Phytochemistry 61, 221-294). In particular, the patent applications (WO 9924561, EP0516958, WO9305160, WO9305159 and WO9712982) disclose different imagined strategies. However, the overexpression or underexpression of one or more enzymes do not always give constant and foreseeable results.

Cinnamate 4-hydroxylase (C4H) exists in at least two forms, depending on the species under consideration. The C4H-1 form is involved in lignification and the metabolism of the phenyl-propanoids, while the role of the C4H-2 form is not yet very clear. Experiments on the deregulation of C4H-1 suggest that this gene is limiting in the formation of lignins, the deregulation apparently resulting in a progressive diminution and a quantitative reduction (SIG ratio) in the lignin.

The patent application EP 1000543 suggests a decrease in the amount of cinnamate 4-hydroxylase (called CA4H in that application) and of cinnamyl alcohol dehydrogenase (CAD) to aldehydes utilizable for improving tolerance to pathogenic fungi. However, this application states that the reduction in C4H alone is insufficient for obtaining this result (paragraph [0057], page 12). Nor does this application describe maize exhibiting a muted C4H gene.

Inter alia, the patent application WO 99/10498 describes the sequence of the maize C4H gene. That application does not describe the obtention of maize plants having a muted C4H gene, exhibiting improved digestibility, increased tolerance to fungal pathogens and acceptable agronomic properties (yield, resistance to lodging . . . ). Nor does that application describe the generation of transgenic plants underexpressing C4H and exhibiting increased tolerance to fungal pathogens.

It is thus difficult for a person skilled in the art to foresee the actual effects of an inhibition of C4H alone or of a specific mutation of C4H on the digestibility of maize, its tolerance to pathogenic fungi and the preservation of agronomic value (yield, resistance to lodging . . . ).

The purpose of the present invention is to provide the person skilled in the art with a maize which effectively has improved digestibility and increased tolerance to fungal pathogens, by the development of a favorable allele of C4H (called D1938), the insertion of a transposon having been effected after the nucleotide 2852 in the gene represented by SEQ ID No.1, which corresponds to the genomic DNA for this enzyme.

The sequence of the cDNA (sequence 27 of WO 99/10498) is represented by SEQ ID No.2, the coding part extending from the nucleotides 53 to 1555 for this sequence. It is clear that these sequences are only given as examples, and that the person skilled in the art is himself capable of identifying the genomic and/or mRNA sequences of C4H for different varieties of maize.

The maize according to the invention exhibits a quantitative and/or qualitative modification of the synthesis of lignin.

"Quantitative modification of the synthesis of lignin" is understood to mean a decrease in the quantity of lignin in the modified maize according to the invention relative to a normal maize (control not modified according to the invention), evaluated for example by measurement of the Klason lignin or of the lignin obtained by acid detergent (acid detergent lignin) by methods well known in the art (see for example Jung et al., J Agric Food Chem., 1999 May; 47(5): 2005-8, Jung et al., J Dairy Sci. 1997 August; 80(8): 1622-8).

"Qualitative modification of the synthesis of lignin" is understood to mean modification of the composition of the lignin of the plant modified according to the invention relative to a control plant (not modified according to the invention), for example a change in the ratio of the S/G subunits or a change in the quality of ferulic acid. The methods for qualitative analysis of lignin are likewise known in the art. NMR can in particular be cited.

Grains possessing the D1938 allele were deposited at NCIMB Limited, Ferguson Building, Craibstone Estate, Bucksburn, Aberdeen, Scotland, AB21 9YA, UK, on 15 Oct. 2007 under the provisions of the Treaty of Budapest, under the number NCIMB 41507.

The invention relates in particular to a maize plant or a maize grain possessing said D1938 allele. The invention also relates to a maize or a maize grain possessing both the D1938 allele and an allele of the CCR1 gene, called Δ3318, said allele Δ3318 being present in a representative sample of grains deposited at NCIMB under the number NCIMB 41236 on 23 Jul. 2004, under the provisions of the Treaty of Budapest. This allele Δ3318 is described in the application WO 2006/035045, incorporated by reference.

This plant displays a disruption/modification of the expression of the C4H gene and/or of the enzyme encoded by this gene such that the lignin content is decreased by at least 5%, and the digestible fraction of the walls is increased by 5%, relative to quasi-isogenic plants not exhibiting this allele resulting in such inhibition of the activity of the C4H gene.

DETAILED DESCRIPTION OF THE INVENTION

Thus, the present invention relates in particular to a maize plant exhibiting an increase in the digestibility (measured by NIRS) of at least 5%, preferably of at least 10%, more preferably of at least 15%.

Preferably, the maize according to the invention is an "elite" maize. The person skilled in the art well knows the definition of an elite maize. Elite maize is understood to mean a maize intended to generate hybrids intended to be marketed by crossing with another elite maize. An elite maize is defined as such in relation to the territory envisaged for marketing and the desired agronomic characteristics) for the hybrid progeny. This is in particular a maize which can be entered into a reference catalogue.

Thus, depending on whether the progeny is intended for human or animal nutrition, respectively a yield of grains, or a yield per hectare and good digestibility, will be sought, when the "elite nature of the maize" is evaluated.

In order to determine the elite character of a maize, hybrids obtained from this are compared with reference commercial hybrids (sold for the same purpose in the same region), by field trials, by reading and measurement of agronomic characteristics appropriate to the desired objective. A maize is defined as elite if the results obtained on the parameters studied for a hybrid obtained by crossing of said maize are greater than 90% of the results found for the same parameters of the reference hybrids. In the context of the present invention, the characteristic of digestibility (digestibility measured by NIRS (near infrared spectroscopy), for example) is in particular studied.

Near infrared spectroscopy (NIRS) is the measurement of the wavelength and the intensity of absorption of near infrared light by a sample, in the regions 800 nm-2.5 µm (12,500-4000 $cm^{-1}$). This spectroscopy is typically utilized for quantitative measurements of organic functional groups, in particular O—H, N—H and C=O. This method is commonly utilized in the analysis of the digestibility of samples.

Thus, an elite maize is a maize combining the maximum of agronomic characteristics necessary for economic penetration of the targeted market. The maize market today being a market of hybrids, the elite nature of the plants is also evaluated in terms of the capacity of said maize for combination/production of hybrids.

Thus, the present invention preferably relates to an elite maize intended for the marketing of hybrids for animal nutrition and silaging, exhibiting the D1938 allele. This elite maize is thus homozygotic for the D1938 allele.

In another embodiment, the invention relates to a hybrid maize obtained by crossing of two homozygotic parent lines, said hybrid maize exhibiting a D1938 allele. This hybrid maize can be homozygotic (if each homozygotic parent exhibits the D1938 allele) or heterozygotic for the D1938 allele.

The invention also relates to a maize or a maize grain, containing one or more transgenes as well as the D1938 allele. Transgenes conferring male sterility, male fertility, resistance to a herbicide (in particular glyphosate, glufosinate, imidazolinone, sulfonylurea, L-phosphinotricine, triazine and benzonitrile), resistance to insects (in particular a transgene coding for a *Bacillus thuringiensis* toxin), or tolerance to water stress may be cited. These maizes can be obtained by crossing a maize containing the allele D1938 with a maize containing said transgene. The implementation of back-crosses followed by self-fertilization makes it possible to obtain an elite maize homozygotic for the allele D1938 and the transgene. However, a maize hybrid simultaneously containing the allele D1938 and the transgene is also included in the scope of the invention.

The present invention also provides the person skilled in the art with means making it possible to select the maize plants possessing these characteristics of improved digestibility and tolerance to pathogenic fungi. In fact it suffices to perform a PCR, or a Southern Blot (hybridization of the genomic DNA on a membrane) to monitor the presence of the insertion in the last exon of the gene coding for C4H. The person skilled in the art can easily determine the primers and probes making it possible to identify the presence of the D1938 allele. The invention thus also relates to a method for monitoring the D1938 allele, by molecular biology techniques and in particular via the PCR utilizing the primers mentioned in the examples.

The invention is also the subject of a process for obtaining maize plants possessing improved digestibility and tolerance to pathogenic fungi thanks to the D1938 allele.

The invention also relates to a method for obtaining a maize line exhibiting better digestibility and tolerance to fungal diseases, comprising the step of introgression of the D1938 allele, into a reference line exhibiting a high grade agronomic characteristic. The introgression of the characteristic is in particular effected by selection, according to the methods known in the art (crossing and self-fertilization). The plants are in particular selected by means of molecular markers.

The principle of this is stated below:

A series of back-crosses is effected between the elite line and the line bearing the D1938 allele (single site on chromosome 5L).

During the back-crosses, it is possible to select individuals bearing the D1938 allele and having recombined the smallest fragment of the donor line around this allele. In fact, using the molecular markers, the individuals having the genotype of the elite line for the markers close to the gene are selected.

In addition, it is also possible to accelerate the return towards the elite parent using molecular markers distributed over the whole of the genome. At each back-cross, the individuals having the most fragments derived from the recurring elite parent will be selected.

With good implementation, from the fourth generation onwards it is possible to obtain a line quasi-isogenic with the elite line, in other words identical to the starting elite line, but having integrated the locus bearing the D1938 allele.

Thus, in a preferred embodiment, said method comprises the steps consisting in:
a) crossing a first maize line exhibiting the D1938 allele with a second maize line not exhibiting said allele,
b) genotyping the progeny obtained and selecting the progeny exhibiting the D1938 allele having the best genome ratio with regard to said second line,
c) back-crossing said progeny with said second maize line,
d) repeating steps b) and c) if necessary until a line isogenic with said second maize line, exhibiting the D1938 allele, is obtained,
e) optionally, performing self-fertilization in order to obtain a plant homozygotic for the D1938 allele.

The genotyping of step b) is preferably performed utilizing molecular markers (microsatellite markers for example), making it possible to define the share of each of the two parents in the progeny. Likewise, in the progeny, the maizes which have the appropriate genetic characteristic as regards the allele D1938 are selected in a standard manner by the methods of molecular biology (such as PCR or Southern Blot).

Surprisingly, it has been shown that the repetition of the back-crosses between the lines selected in step b) and the second maize makes it possible to achieve the appearance of a much more pronounced phenotype within said second maize.

This result is quite surprising as one could have expected to observe an improvement in the digestibility from the first crossing of the maize exhibiting the allele D1938 with the second maize.

The invention also relates to a method wherein the allele Δ3318 is also introgressed into the maize into which the allele D1938 is introgressed. The introgression of Δ3318 is in particular effected according to the teachings of WO 2006/035045, utilizing in particular the primers described in the examples of that application.

Moreover, the agronomic results observed after multiple back-crosses (5 back-crosses and 2 self-fertilizations) do not show any difference between the isogenic lines exhibiting the mutation and the control plants.

More generally, the invention also relates to a method for increasing the tolerance to a fungal pathogen in maize comprising a step consisting in qualitatively and/or quantitatively modifying the synthesis of lignins, by the total or partial inhibition of the expression of the gene coding for cinnamate 4-hydroxylase (C4H), the tolerance to said fungal pathogen being increased relative to a non-modified maize. The sequence of one allele of the C4H gene is SEQ ID No.1, the cDNA being represented by SEQ ID No.2.

It should be noted that the sequences provided in the list of sequences must only be regarded as illustrations of this allele. It is clear that the person skilled in the art, utilizing these sequences, is capable of isolating this C4H gene for other varieties of maize, in particular by isolating, in the genome of another variety, the allele in question by PCR, or Southern Blot, then sequencing it.

The inhibition of the C4H gene can be achieved by any means known in the art. Thus, the mutation of the genes can be effected by insertion of a transposable element or of a transfer DNA (T-DNA). Physical or chemical mutagenesis can also be effected, in particular by the use of EMS, Xrays or ultraviolet.

The plants thus mutated are screened for example by PCR, utilizing primers situated in the target gene. However, it is also possible to utilize other screening methods, such as Southern Blots or screening via the AIMS method described in WO 99/27085 (for detecting insertions), by utilizing probes specific for the target genes, or methods for detecting point mutations or small insertions/deletions utilizing particular endonucleases (Cel I, Endo I) such as are described in WO 2006/010646.

In another embodiment, the inhibition is achieved by transformation of the plant with a vector containing a sense or antisense construct of the target gene. These two methods are known for enabling, under certain conditions, the inhibition of the target gene. The RNA interference method (RNAi), which is particularly effective for the silencing of genes in plants, is also utilized. This method is well known to the person skilled in the art and consists in the transformation of the plant with a construct producing, after transcription, a double-strand duplex of RNA, one of the strands whereof is complementary to the mRMA of the target gene.

Finally, the invention relates to the utilization of a maize according to the invention for the preparation of a composition intended for animal nutrition, to a method for the preparation of a composition intended for animal nutrition comprising the silaging of a maize according to the invention, and to the composition intended for animal nutrition thus obtained. In particular, said maize is particularly useful for the nutrition of livestock.

EXAMPLES

Example 1

Description of a Maize Exhibiting a Modification in the C4H Gene

Figure 1:
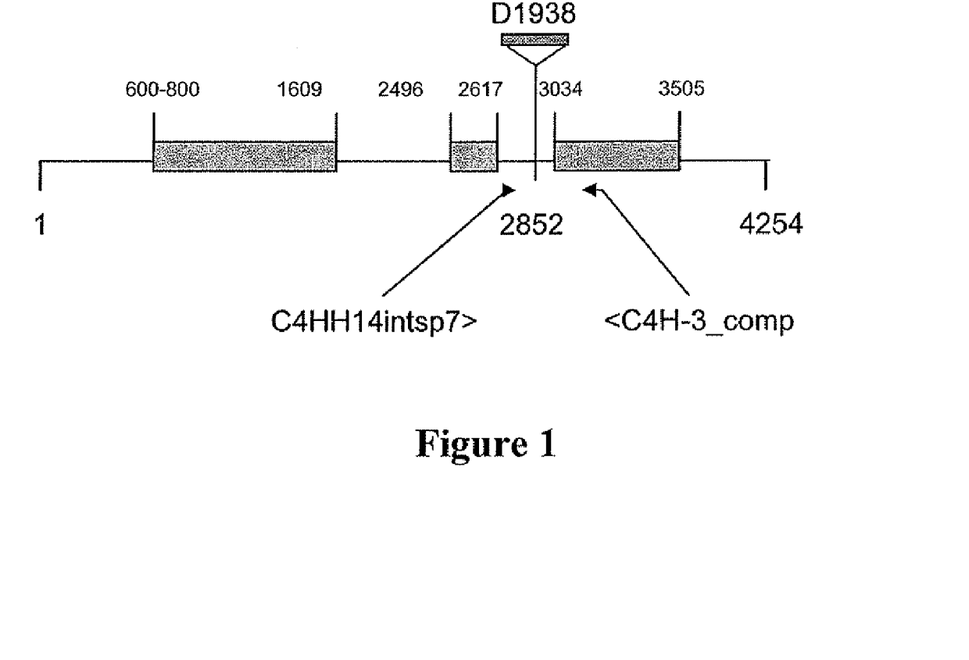
FIG. 1 shows a diagrammatic representation of the insertion of the C4H gene into the second intron. The gray blocks correspond to exons, the dashes correspond to introns. The position of two primers C4HH14intsp7 and C4H-3_comp enabling monitoring of the presence of the insertion is shown.

A maize line exhibiting an insertion of a transposable element at position 2852 of the reference sequence SEQ ID No.1 is isolated (FIG. 1). The allele thus obtained is called D1938.

Although it is present in an intron, it is supposed that this insertion has the effect of deregulating the transcription and/or the translation of the C4H gene, or the stability of the mRNA of C4H, leading to a decrease in the activity of the enzyme in the presence of the D1938 allele, as evidenced by the biochemical results for lignin composition and content (Example 2).

In order to determine whether the insertion is in homozygotic or heterozygotic form, a pair of primers was defined: a sense primer C4HH14intsp7 of sequence SEQ ID No.3: CACGTCTTAATCAAGTCTCCG and an antisense primer C4H-3_comp of sequence SEQ ID No.4: GTTCAT-GTGGGGGACCAGCAGC.

In addition to these two primers, the specific primer of the endogenous transposable element, OMuA (SEQ ID No.5): CTTCGTCCATAATGGCAATTATCTC, is utilized. This primer is directed towards the end of the transposon.

These three primers can be utilized simultaneously in a PCR amplification experiment starting from genomic DNA (hybridization temperature=58° C.). Deposition of the amplification products onto gel reveals:

the obtention of a single band of about 530 bp length for so-called wild plants at this locus (in other words not having the mutation), the obtention of two bands of about 150 bp and 420 bp for homozygotic mutant plants, corresponding to the amplifications obtained with the primers present in the gene and in the transposon (due to the insertion, amplification with the primers C4HH14intsp7 and C4H-3_comp is impossible as too long), or the obtention of all three of the bands for heterozygotic plants.

Figure 2:
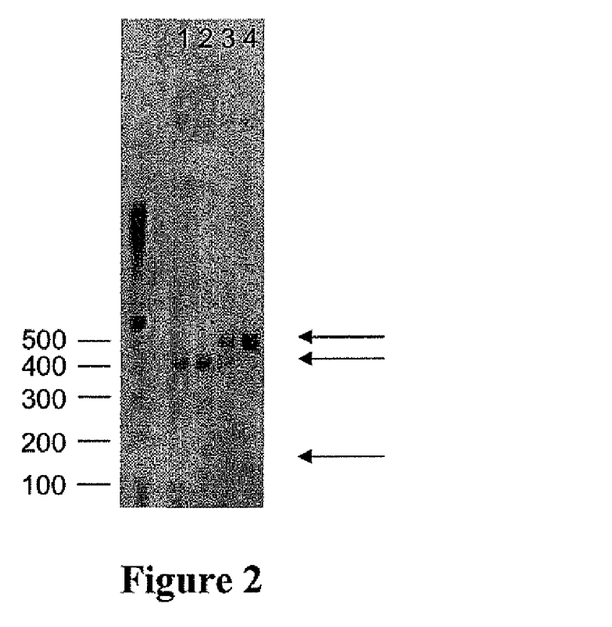
FIG. 2 shows an illustration of a method enabling the monitoring of the introgression of the D1938 allele. Amplification results on agarose gel.

These results are illustrated in FIG. 2.

The furthest left well on the gel contains the size marker; the lowest band corresponds to 100 bp and there are 100 bp between each band.

Wells 1 and 2 correspond to mutant individuals homozygotic for D1938.

Well 4 corresponds to a wild individual not bearing the D1938 allele.

Well 3 corresponds to a heterozygotic individual.

Example 2

Phenotype Analysis of the Mutant D1938 for the Characteristic Digestibility

In order to study more precisely the effect of the insertion observed in the C4H gene in an elite maize, successive backcrosses were effected with an elite maize line.

This method makes it possible very rapidly to obtain quasi-isogenic lines differing only by the locus bearing the modified allele, the progeny being tested for the possession of a genome ratio as close as possible to that of the elite parent while having the allele which it is desired to introgress. These tests are assisted by molecular markers (well known techniques, microsatellites, AFLP . . . ). To attempt to assess the effect of the insertion as early as possible (obtention of homozygotic plants), self-fertilizations are performed at different intermediate back-cross stages.

Figure 3:
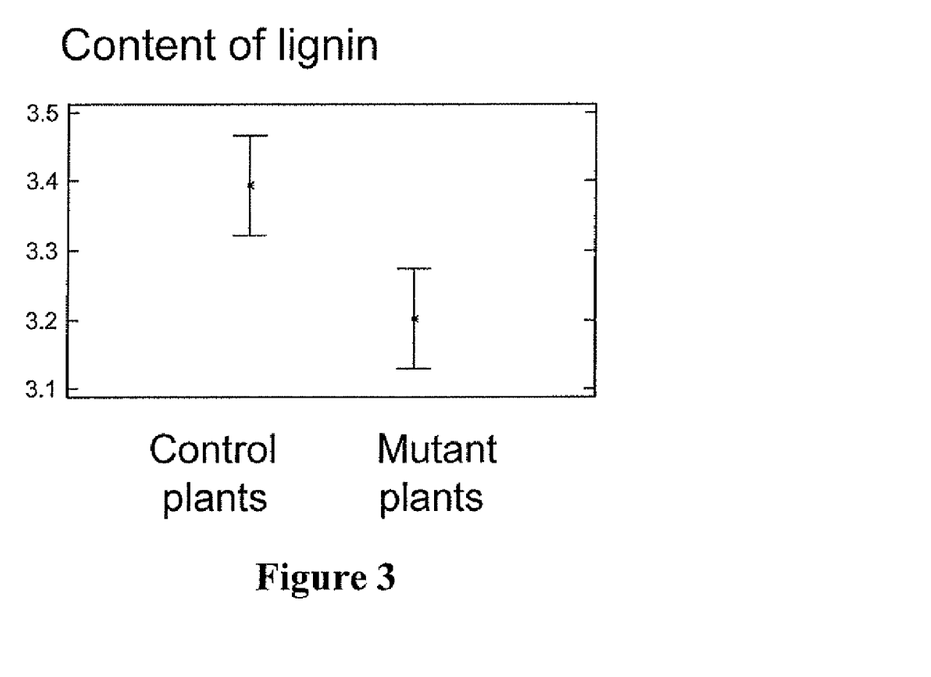
FIG. 3 shows NIR results of the introgression of the D1938 allele on the quantity of lignin. Mutant plants: possessing the D1938 allele; control plants: plants not possessing that allele.
Figure 4:
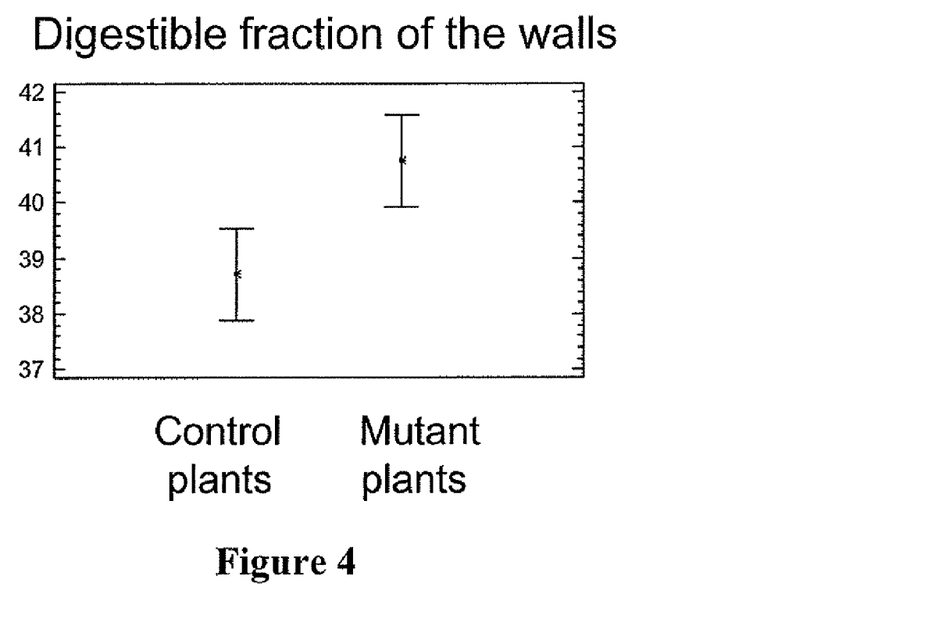
FIG. 4 shows measurement of the effect of the D1938 allele on the digestible fraction of the walls. Mutant plants: possessing the D1938 allele; control plants: plants not possessing that allele.

FIGS. 3 and 4 display wall NIR and digestibility results obtained on BC5S2 plants (5 back-crosses and 2 self-fertilizations).

This shows that the introgression of the D1938 allele makes it possible to achieve a decrease in the quantity of lignin (acid detergent lignin) after isolation of the walls (neutral detergent fibers), by the methods known to the person skilled in the art.

The differences observed between the control and mutant plants are statistically significant.

The results are summarized in the following table:

|  | Control plants (mean) | Mutant plant (means) |
|---|---|---|
| Lignin content = ADL | 3.39 | 3.20 |
| Digestible fraction of walls | 38.71 | 40.75 |

Example 3

Phenotype Analysis of the Mutant D1938 Maize for the Characteristic of Resistance to Fungal Diseases A homozygotic mutant plant and a wild homozygotic control are available for each insertion event. Given the levels of introgression of the mutation, it can be considered that the mutant and the wild differ only by the presence or absence of the mutation. The experiment is performed according to the following protocol:

2 locations 3 repetitions per location artificial inoculation with *Fusarium monoliforme* scoring of the symptoms observed on cobs (score from 1 to 7). This is a visual scoring of the intensity of attack on cobs: the attack intensity score is calculated from the percentage of the area of the cob attacked by the pathogen (Reid et al., Agriculture and Agri-Food Canada, Ottawa, Ont. Technical Bulletin 1996-5E. 40 pp). The scores correspond to: 1=0% attacked, 2=1-3%, 3=4-10%, 4=11=25%, 5=26-50%, 6=51-75% and 7=76-100%.

In the following examples, the "locations" repetitions have been converted to "simple repetitions" in order to perform a simple statistical analysis.

The statistical analysis was performed on each mutant so as to know whether there is a difference between mutant (M) and wild or control (W).

The results demonstrate that the presence of the allele D1938 of the gene C4H increases the tolerance to an infection with *Fusarium monoliforme*.

| TYPE | Number | Means | Standard Deviations |
|---|---|---|---|
| M | 72 | 2.9163 | 0.124743 |
| W | 81 | 3.8593 | 0.117351 |
| Contrast | Difference |  | ±limits |
|  | *−0.942997 |  | 0.338582 |

*statistically significant difference

These results demonstrate that modification of the expression of the C4H gene makes it possible to decrease the symptoms observed after infection by *Fusarium*, and thus to improve the tolerance of the plants to this pathogen.

Example 4

Creation of Transgenic Plants Bearing an Expression Cassette Enabling Inhibition of a C4H Gene a—Transformation of maize plants with *Agrobacterium tumefaciens* by a C4H antisense construct.

The transformation of maize with *Agrobacterium tumefaciens* is performed by means of a vector in the form of a plasmid of about 50 kb obtained by recombination in *Agrobacterium* between a pBIOS vector and a superbinary vector (pSB1). This vector comprises in particular: a plasmid replication origin Col EI, necessary for the maintenance and the multiplication of the plasmid in *Escherichia coli*, not functional in *A. tumefaciens*, a replication origin functional in *A. tumefaciens*, the supplementary regions virB, virC and VirG of *A. tumefaciens* which increase the efficiency of transformation, and genes for resistance to tetracycline (tetra) and spectinomycin (spect) under control of promoters expressing only in the bacteria.

A transfer DNA (T-DNA) bearing two expression cassettes is introduced into this vector. The first cassette comprises: the promoter sequence of CsVMV (WO 97/48819), a sequence derived from the C4H sequence of maize in antisense orientation (SEQ ID No.1) and the NOS (nopaline synthase) terminator sequence. The second cassette comprises: the rice actin gene promoter sequence and the sequence of the first intron of that gene, a gene for selection with a herbicide and an NOS terminator sequence.

The transformation is effected via the transformation protocol of Ishida et al. (Nature Biotechnology, 14, 745-750, 1996) for transformation with *A. tumefaciens*.

Immature cobs of a line produced under glass are taken 10 days after pollination and sterilized for 15 mins. The embryos are taken and placed in contact with a suspension of *Agrobacterium* containing the vector described above for 5 mins. After removal from the suspension of *Agrobacterium*, the embryos are cultured on a medium containing neither bacteriostatic nor selective agent. This co-culturing takes place in the dark for 4 to 7 days. After the co-culturing, the embryos are pricked out again on a fresh callogenesis medium containing the bacteriostatic and the selective agent. A callus initiates and develops from the transformed cells of these embryos. The callogenesis step takes place at 25° C. in the dark and lasts 5 weeks. The callus embryos are pricked out again on fresh medium every 2 to 3 weeks. At the end of this stage, the calluses are pricked out again on a regeneration medium for 5 weeks with repricking of the callus onto fresh medium after 2 to 3 weeks, Regeneration of plantlets is effected from the calluses, which are subjected to rooting in tubes once they are sufficiently developed. After 10-15 days in tube, the plantlets are acclimatized in a phytotron before being transferred to the greenhouse. The transformants are then cultivated and crossed with pollen from a non-transgenic plant to produce the T1 generation.

b—Transformation of maize plants with *Agrobacterium tumefaciens* by an RNAi construct for the C4H gene.

Construction of a vector containing a fragment of the sequence of the C4H gene in sense and antisense orientation. This vector is constructed utilizing a fragment from 200 to 700 bp derived from the C4H sequence using the Gateway system (Invitrogen). This vector bears in particular an expression cassette made up of the promoter CsVMV, the fragment from the C4H sequence in antisense orientation, the first intron of the rice tubulin gene, the fragment from the C4H sequence in sense orientation and the NOS terminator.

This vector is utilized for the transformation of maize by the method of Ishida described above.

c—Phenotype analyses of the anti-sense and RNAi transformants

The protocol for analysis by NIRs according to Example 2 is utilized for evaluation of the digestibility. The tolerance to the *Fusaria* is evaluated according to the protocol for artificial inoculation with *Fusarium monoliforme* described in Example 3.

Example 5

Search for New Alleles for the C4H Gene in the Genetic Resources or in a Collection of Mutations Induced in Maize by a Chemical Agent A representative collection hereinafter referred to as "core collection" presenting maximal molecular variability with regard to both geographical and temporal criteria of origin is utilized in order to identify new alleles of the C4H gene by the so-called EcoTilling method described in the literature (Mejlhede et al., 2006, Plant Breeding, 125: 461-467).

Simultaneously with the screening of the "core collection", a search for "induced alleles" is performed starting from a maize collection derived from the merging of maize collections mutated with ionizing radiation or a chemical agent (EMS). This maize collection makes it possible to identify alleles not naturally present in the maize varieties existing naturally. Moreover, 5% of the mutations discovered are null alleles of C4H genes, in other words an allele of the C4H gene where the function is annulled (absence of expression). This so-called TILLING (Targeting Induced Local Lesions IN Genomes) method is described in the literature (McCallum et al. 2000, Nature Bio-technology, 18: 455-457).

The alleles derived from the Tilling or Ecotilling approaches are identified using the technology developed by Henikoff and Comaï (Plant J. 2006 February; 45(4): 684-94, Annu Rev Plant Biol. 2003; 54: 375-401). For this, specific primers of the CCR1 gene are developed. The PCR product corresponding to the amplification of one copy of the C4H gene is next compared with an identical PCR product derived from a DNA derived from a reference variety. The mutations analysis method is effected by identification of DNA heteroduplexes created by the renaturation of DNA strands deriving from the copy of the variety tested and the reference variety. If a mutation is present in the variety tested, a pairing anomaly (or "mismatch") ensues. This anomaly is detected then cleaved with an enzyme of the endonuclease type recognizing that particular structure (for example the enzyme CelI or the enzyme EndoI). The recognition of the mismatch is then detected by electrophoresis. For example, on agarose gel, on an automatic on-plate sequencer (LICOR type) on a capillary sequencer on ABI3100 or on ABI3730.

Each difference detected constitutes a specific "haplotype" of the C4H gene. The group of varieties exhibiting distinct haplotypes (deriving either from screening of genetic resources or from the discovery of artificially induced mutations) are crossed with a reference variety so as to have available a collection of alleles of C4H in a single elite genetic base.

Phenotype analyses are undertaken to determine whether the presence of a particular haplotype is correlated to the characteristic digestible or to resistance to fusariosis.

Example 6

Utilization of the Identified Alleles in Varietal Selection

The haplotypes conferring the strongest level of digestibility and of resistance/tolerance to fusariosis are then utilized in varietal selection. Genetic mixing between the resistant/tolerant variety and varieties exhibiting other agronomic qualities such as high yields, high protein levels and capacity for resistance to preharvest sprouting, etc. makes it possible to select new varieties combining the group of desired characteristics. The allele conferring resistance to fusariosis is followed by molecular labeling in the course of this process of varietal selection.

Thus the alleles identified by Tilling or EcoTilling or validated by association test make it possible to propose crossing plans between the most complementary individuals on the basis of their alleles (here one or more alleles conferring resistance to fusariosis) then to utilize the knowledge accumulated for proposing pertinent crossings of potential parents in order to pyramid genes (accumulate various haplotypes) that should lead to the obtention of improved varieties.

The invention claimed is:

1. A maize plant exhibiting an allele of the C4H gene, called D1938, containing an insertion of a transposon after nucleotide 2852 of SEQ ID No.1, said allele being present in a representative sample of grains deposited at NCIMB under the number NCIMB 41507.

2. The maize plant as claimed in claim 1, further comprising an allele of the gene CCR1, called Δ3318, said allele being present in a representative sample of grains deposited at NCIMB under the number NCIMB 41236.

3. A maize grain exhibiting an allele of the C4H gene, called D1938, containing an insertion of a transposon in the first intron of said gene, said allele being present in the grains deposited at NCIMB under the number NCIMB 41507.

4. The maize grain as claimed in claim 3, further comprising an allele of the CCR1 gene, called Δ3318, said allele being present in a representative sample of grains deposited at NCIMB under the number NCIMB 41236.

5. A method for obtaining a maize plant exhibiting increased digestibility, comprising the introgression of an allele of the C4H gene, called D1938 into said maize plant, comprising:
   a) crossing a first maize line exhibiting the an allele of the C4H gene, called D1938, containing an insertion of a transposon after nucleotide 2853 of SEQ ID No. 1, said allele being present in a representative sample of grains deposited at NCIMB under the number NCIMB 41507, with a second maize line not exhibiting said allele,
   b) genotyping the progeny obtained and selecting the progeny exhibiting the D1938 allele, and having the best genome ratio with regard to said second maize,
   c) back-crossing said progeny with said second elite maize line utilizable for the production of hybrids,
   d) repeating steps b) and c) if necessary until a line isogenic with said second maize, exhibiting the D1938 allele, is obtained,
   e) optionally, performing self-fertilization in order to obtain a plant homozygotic for the D1938 allele.

6. A method for obtaining a maize plant exhibiting increased tolerance to a pathogenic fungus, comprising the introgression of the D1938 into said maize plant, comprising:
   a) crossing a first maize line exhibiting an allele of the C4H gene, called D1938, containing an insertion of a transposon after nucleotide 2853 of SEQ ID No. 1, said allele being present in a representative sample of grains deposited at NCIMB under the number NCIMB 41507, with a second maize line not exhibiting said allele,
   b) genotyping the progeny obtained and selecting the progeny exhibiting the D1938 allele, and having the best genome ratio with regard to said second maize,
   c) back-crossing said progeny with said second elite maize line utilizable for the production of hybrids,
   d) repeating steps b) and c) if necessary until a line isogenic with said second maize, exhibiting the D1938 allele, is obtained,
   e) optionally, performing self-fertilization in order to obtain a plant homozygotic for the D1938 allele.

7. The method as claimed in claim 6, wherein said fungal pathogen is of the *Fusarium* genus.

8. The method as claimed in claim 5, further comprising introgressing the allele Δ3318 into said maize plant.

9. A method for the preparation of a composition intended for animal nutrition comprising silaging of the maize plant as claimed in claim 1.

10. A method for increasing the tolerance to a fungal pathogen in maize comprising qualitatively and/or quantitatively modifying the synthesis of lignins, by the total or partial inhibition of the expression of the gene coding for cinnamate 4-hydroxylase (C4H), the tolerance to said fungal pathogen being increased relative to an unmodified maize.

11. The method as claimed in claim 10, wherein the inhibition is achieved by mutation of said gene by insertion of a transposable element or of a T-DNA or by physical mutagenesis.

12. The method as claimed in claim 10, wherein the inhibition is achieved by transformation of said plant by an antisense construct or overexpression, or RNAi.

13. The method as claimed in claim 6, further comprising introgressing the allele Δ3318 into said maize.

14. The method as claimed in claim 7, further comprising introgressing the allele Δ3318 into said maize.

15. A method for the preparation of a composition intended for animal nutrition comprising silaging of the maize plant as claimed in claim 2.

* * * * *

SEQUENCE LISTING

<160> NUMBER OF SEQ ID NOS: 5

<210> SEQ ID NO 1
<211> LENGTH: 4254
<212> TYPE: DNA
<213> ORGANISM: Zea mays

<400> SEQUENCE: 1

```
catgtgtagg aacttctaat tggcctctta aggatggaca tctttcatca atttattaga      60
tttagtgaga ggctccaaga tggtatatgt agaatgggag gtaaagacaa actttggcca     120
gtttacattt tcaaaactac aactatatat cttgcctatc cttgtttact ataaataaga     180
gtggtaatgg atcacgatcc aaatgttttt cgtaatttat ttgtgccttt aattaatatt     240
agttcaaaat tgaatagaat tagagtccaa tcttaatcga tctgacactt aaaattttta     300
gtgtaaaatt tagagtcatt accaccccta actataagaa cccatcacag tccacttatc     360
tgcacattct ctaattttgt tctgtgaatt agctgaagca tttttgtaag gacttggctg     420
```

```
cgtttcgtaa ttagtaacag taaacttttc catggaaaag acgggttagc ggagctgcaa    480
cttcaccgac tgcagtctca gcggtgatcc atgaatcccc tttgggcctt ccgctgccag    540
caaatagcaa tagtagtgtt tgatcccgtt ccaaaaacaa aaacaaaaag aagagccaca    600
cattttggaa acttttttgt ggggcccgcc cgcagcacca aaaccatacc aaccccgca     660 atggcaaacc aaacaaattc gtgtactcaa attggacccg tctcggcgct ctctcccaaa    720
aaaacgctat aaaatcccg gcattcctcc ttgcctgttc catcgcctcc acgaacaaac     780
cacacacccc acctaccccg gccggaccgg caggcagcac agcatggacc tcgccctcct    840
agagaaggcc ctgctgggcc tgttcgccgc ggctgtggtg gccatcgccg tggccaagct    900
gaccggcaag cggtaccgcc tcccaccggg gcccccgggc gccccgtgg tgggaaactg     960 gctgcaggtg ggcgacgacc tgaaccaccg caacctgatg ccatggcga agcggttcgg    1020 cgacatcttc ctgctgcgca tgggcgtgcg caacctggtg gtggtgtcga ccccggagct    1080
ggccaaggag gtgctccaca cgcagggcgt ggagttcggc tcccgcaccc gcaacgtggt    1140
gttcgacatc ttcacgggca aggggcagga catggtgttc acggtgtacg cgaccactg     1200 gcgcaagatg cggcgcatca tgaccgtccc cttcttcacc aacaaggtgg tggcccagaa    1260
ccgcgccggg tgggaggagg aggcccggct ggtggtggag gacgtgagga aggaccccga    1320
ggccgcggcc ggcggcgtcg tgctccgccg ccgcctccag ctgatgatgt acaacgacat    1380
gttccgcatc atgttcgacc gccggttcga cagcgagcac gacccgctct tcaacaagct    1440
caaggcgctc aacgcggagc gcagccgcct gtcgcagagc ttcgagtaca actacgcga     1500 cttcatcccc gtgctccgcc ccttcctccg cggctaccct aaccgctgcc acgacctcaa    1560
gacgcgccgc atgaaggtct tcgaggacaa cttcgtacag gagcgcaagt aagtctgcca    1620
tattccattt tctttccttt cctttttctt ttgagctggc cacctgggct ggtggttggt    1680
tgacggcggg tggagttgca agttgcatcg tcggcgggtg aggtatgagc tggaggctgg    1740
agctgggcgg aagacagttg catgcattgc atctgtgcct ctgtggtggt ggctgcgcac    1800
atgctgcaac cgatgccatc taccggtgga caaatcaatg ccatctgcca gtggacaagg    1860
acgaatcaac agccaagtcc atattttatt ttattttgct agtcattgaa ttttggcgag    1920
atcggacgac ttttgtgatg catggctggc tccagtcatg tttgacacgt aactaaaaga    1980
cccaccgcac gggttaggga gtactagtac ctactactcc taaacaacaa cttgtagttg    2040
tccacaacag gttaacagat caaagaagga taggtgagcg gcactactca tctcgtggct    2100
tccggtgaca gatgatcagc ccacgaagga aaaagaaaaa gggactcgct tgatttgcgt    2160
tgctttgctt ccgcgcaag gccgaaagct taaggtcggg gcaacgacac accgagagcg     2220
acggagatat accacgctct gctgcttcat gatagctgga aggacatcag catgacacgc    2280
atgccaataa tgtagtagaa gactagttta tttgtcacct actaggcaga gagtgcggtg    2340
gttccatgaa ccaaccattc gtgcgtgcgt gcccaccgca cgaccacgag ggggcatgca    2400
acatatactt tacaaaattc attcggttgt tgacttggtt tcaattcatt gggttgggaa    2460
gacaaaacta acatggatgc gttgcgtact cacaggaagg tgatggctca gactggtgag    2520
atccggtgcg ccatggatca catcctcgag gccgagagga agggcgagat caaccacgac    2580
aacgtcctct catcgtcga gaacatcaac gtcgcaggta tcgataatcg tcactgctca    2640
gtgcaatgaa acgaaacag agtatgctat gtctgaagaa ccaagtgaga cttatcattc     2700
aactactgca gtccagcgct actacacaaa caaatagcac tgcaatatcg gaagatataa    2760
taatataagg cacgtcttaa tcaagtctcc gtcagccaac ttaattccgt ccttaattaa    2820
```

| | |
|---|---|
| ccggcaacat actgagccta atgcggtgtc acacttcaag tgggctcccg tatttatctg | 2880 |
| ctaggcatag tatctatctg tgtatcaaaa ggtagttgaa gccgccacca cgtgaccacg | 2940 |
| cctcaaaaag aattgcgttt tgatttgtat atccaagctg ccacacctgc aggcagtcgg | 3000 |
| tggcaaaaaa aaaaaactaa tttgtttgct tttgcagcga tcgagacgac gctgtggtcg | 3060 |
| atcgagtggg gcatcgccga gctggtgaac cacccggcca tccagcacaa gctccgggag | 3120 |
| gagctcgcct cggtgctggg cgccggcgtg cctgtgacgg agccggacct cgagcgcctc | 3180 |
| ccctaccttc aggccatcgt caaggagacg ctccgcctgc gcatggccat cccgctgctg | 3240 |
| gtcccccaca tgaacctcaa cgacggcaag ctcgccggct tcgacatccc cgccgagtcc | 3300 |
| aagatcctcg tcaatgcctg gttcctcgcc aacgacccca agaggtgggt gcgccccgac | 3360 |
| gagttccggc ccgagcgctt cctggaggag gagaagtccg tggaggccca cggcaacgac | 3420 |
| ttccgattcg tgcccttggg ggtcggccgc cggagctgcc ctgggatcat cctcgcgctg | 3480 |
| cctatcatcg gcatcaccct gggccggctg gtgcagaact tccagctgct gccgccgccg | 3540 |
| gggctggaca agatcgacac cacggagaag cccggccagt tcagcaacca gatcgccaag | 3600 |
| catgccacca tcgtctgcaa gccctcgag gcctagaaat caatgcgtgt ttcctgcacg | 3660 |
| cgccccgca gatgaagcac tatgtatttt ctcttttttt tgtgtgttgt gtttttttta | 3720 |
| ctaagaggag atgtatttct tgttcgtaaa atgcacttag tcaaatggat cgagattatg | 3780 |
| ttgatcatta aacaccaaaa tcacttagtc aaacgggtcg ggatccattt tcctcacaat | 3840 |
| gtcaaccttt gactgatgac aatataatca agcaagcaa atattaaata aaaaaatatg | 3900 |
| tactctactt gcaatagatg catgtgcata tgcaacgtgt atgagaaact aaattgatag | 3960 |
| atatgcggtc atttagagca tataggaaga catgttaaag tatacacgaa gctatcaaat | 4020 |
| acttgccctc taaaatattt ctctccctaa aagaaagttc tccacatttg gaaaaacagt | 4080 |
| ctctccettt gaggaaaagg acatacaccc cctattggaa aactctcttt caatacaaga | 4140 |
| ggaaaaaaag acaagaatga atagactaac tcccccttaat ttatgcatag ttaaatggta | 4200 |
| aaggatattc tagtgatacc aaataaagaa tttaaaagca tatgcatatg tagg | 4254 |

<210> SEQ ID NO 2
<211> LENGTH: 1669
<212> TYPE: DNA
<213> ORGANISM: Zea mays

<400> SEQUENCE: 2

| | |
|---|---|
| cgaacaaacc acacacccca cctacccagg ccggaccggc aggcagcaca gcatggacct | 60 |
| cgccctccta gagaaggccc tgctgggcct gttcgccgcg gctgtggtgg ccatcgccgt | 120 |
| ggccaagctg accggcaagc ggtaccgcct cccaccgggg cccccgggcg ccccgtggt | 180 |
| gggaaactgg ctgcaggtgg gcgacgacct gaaccaccgc aacctgatgg ccatggcgaa | 240 |
| gcggttcggc gacatcttcc tgctgcgcat gggcgtgcgc aacctggtgg tggtgtcgac | 300 |
| cccggagctg gccaaggagg tgctccacac gcagggcgtg gagttcggct cccgcacccg | 360 |
| caacgtggtg ttcgacatct tcacgggcaa ggggcaggac atggtgttca cggtgtacgg | 420 |
| cgaccactgg cgcaagatgc ggcgcatcat gaccgtcccc ttcttcacca acaaggtggt | 480 |
| ggcccagaac cgcgccgggt gggaggagga ggcccggctg gtggtggagg acgtgaggaa | 540 |
| ggaccccgag gccgcggccg gcggcgtcgt gctccgccgc cgcctccagc tgatgatgta | 600 |
| caacgacatg ttccgcatca tgttcgaccg ccggttcgac agcgagcacg acccgctctt | 660 |
| caacaagctc aaggcgctca acgcggagcg cagccgcctg tcgcagagct tcgagtacaa | 720 |

```
ctacggcgac ttcatccccg tgctccgccc cttcctccgc ggctacctca accgctgcca      780
cgacctcaag acgcgccgca tgaaggtctt cgaggacaac ttcgtacagg agcgcaagaa      840
ggtgatggct cagactggtg agatccggtg cgccatggat cacatcctcg aggccgagag      900
gaagggcgag atcaaccacg acaacgtcct ctacatcgtc gagaacatca acgtcgcagc      960
gatcgagacg acgctgtggt cgatcgagtg gggcatcgcc gagctggtga accacccggc     1020
catccagcac aagctccggg aggagctcgc ctcggtgctg ggcgccggcg tgcctgtgac     1080
ggagccggac ctcgagcgcc tcccctacct tcaggccatc gtcaaggaga cgctccgcct     1140
gcgcatggcc atcccgctgc tggtccccca catgaacctc aacgacggca agctcgccgg     1200
cttcgacatc cccgccgagt ccaagatcct cgtcaatgcc tggttcctcg ccaacgaccc     1260
caagaggtgg gtgcgccccg acgagttccg gcccgagcgc ttcctggagg aggagaagtc     1320
cgtggaggcc cacggcaacg acttccgatt cgtgcccttt ggggtcggcc gccggagctg     1380
ccctgggatc atcctcgcgc tgcctatcat cggcatcacc ctgggccggc tggtgcagaa     1440
cttccagctg ctgccgccgc cggggctgga caagatcgac accacggaga gcccggcca      1500 gttcagcaac cagatcgcca agcatgccac catcgtctgc aagcccctcg aggcctagaa     1560
atcaatgcgt gtttcctgca cgcgcccccg cagatgaagc actatgtatt ttctcttttt     1620
tttgtgtgtt gtgttttttt tactaagagg agatgtattt cttgttcgt                1669

<210> SEQ ID NO 3
<211> LENGTH: 21
<212> TYPE: DNA
<213> ORGANISM: Artificial
<220> FEATURE:
<223> OTHER INFORMATION: Synthetic primer C4HH14intsp7

<400> SEQUENCE: 3
cacgtcttaa tcaagtctcc g                                                 21

<210> SEQ ID NO 4
<211> LENGTH: 22
<212> TYPE: DNA
<213> ORGANISM: Artificial
<220> FEATURE:
<223> OTHER INFORMATION: Synthetic primer C4H-3_comp

<400> SEQUENCE: 4
gttcatgtgg gggaccagca gc                                                22

<210> SEQ ID NO 5
<211> LENGTH: 25
<212> TYPE: DNA
<213> ORGANISM: artificial
<220> FEATURE:
<223> OTHER INFORMATION: Synthetic primer OMuA

<400> SEQUENCE: 5
cttcgtccat aatggcaatt atctc                                             25
```